(12) United States Patent
Niwa

(10) Patent No.: US 11,839,013 B2
(45) Date of Patent: Dec. 5, 2023

(54) RADIATION IMAGING APPARATUS, RADIATION IMAGING SYSTEM AND CONTROL METHOD OF RADIATION IMAGING APPARATUS

(71) Applicant: CANON KABUSHIKI KAISHA, Tokyo (JP)

(72) Inventor: Hiroaki Niwa, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/873,501

(22) Filed: Jul. 26, 2022

(65) Prior Publication Data

US 2023/0036641 A1 Feb. 2, 2023

(30) Foreign Application Priority Data

Jul. 28, 2021 (JP) ................................. 2021-123016

(51) Int. Cl.
*H05G 1/30* (2006.01)
*A61B 6/00* (2006.01)
*G01T 1/02* (2006.01)

(52) U.S. Cl.
CPC ................. *H05G 1/30* (2013.01); *G01T 1/02* (2013.01)

(58) Field of Classification Search
None
See application file for complete search history.

(56) References Cited

U.S. PATENT DOCUMENTS

| 10,729,393 B2* | 8/2020 | Fujiyoshi ............. A61B 6/4233 |
| 2013/0223592 A1* | 8/2013 | Sato ....................... A61B 6/542 378/97 |
| 2013/0251106 A1* | 9/2013 | Tajima ................. A61B 6/4233 378/97 |
| 2015/0036802 A1* | 2/2015 | Tajima ................. A61B 6/4208 378/62 |
| 2015/0055752 A1* | 2/2015 | Takahashi ................ H04N 5/32 378/91 |

(Continued)

FOREIGN PATENT DOCUMENTS

| JP | 2013-52151 A | 3/2013 |
| JP | 5706279 B2 | 4/2015 |
| JP | 2016-171917 A | 9/2016 |

*Primary Examiner* — Hoon K Song
(74) *Attorney, Agent, or Firm* — VENABLE LLP

(57) ABSTRACT

The radiation imaging apparatus is provided that includes a radiation detector including a pixel array in which a plurality of pixels being capable of detecting radiation as electric signals are arranged, the radiation transmitted through an AEC sensor used for performing automatic exposure control of radiation irradiated from a radiation generating apparatus, a notifying unit for performing threshold value reached notification to the radiation generating apparatus, if a dose value of the radiation incident on the pixel array reaches a threshold value, and a threshold value setting unit for setting the threshold value in second radiation imaging in which automatic exposure control of the radiation by the radiation detector is performed after first radiation imaging in which the automatic exposure control of the radiation by the AEC sensor is performed, based on pixel values related to the electric signals detected by the plurality of pixels in the first radiation imaging

15 Claims, 7 Drawing Sheets

(56) References Cited

U.S. PATENT DOCUMENTS

2016/0025865 A1* 1/2016 Wayama ................ A61B 6/542
                                                  250/370.07
2019/0059845 A1* 2/2019 Osugi .................... G16H 30/20
2019/0391629 A1   12/2019 Yokoyama et al.

* cited by examiner

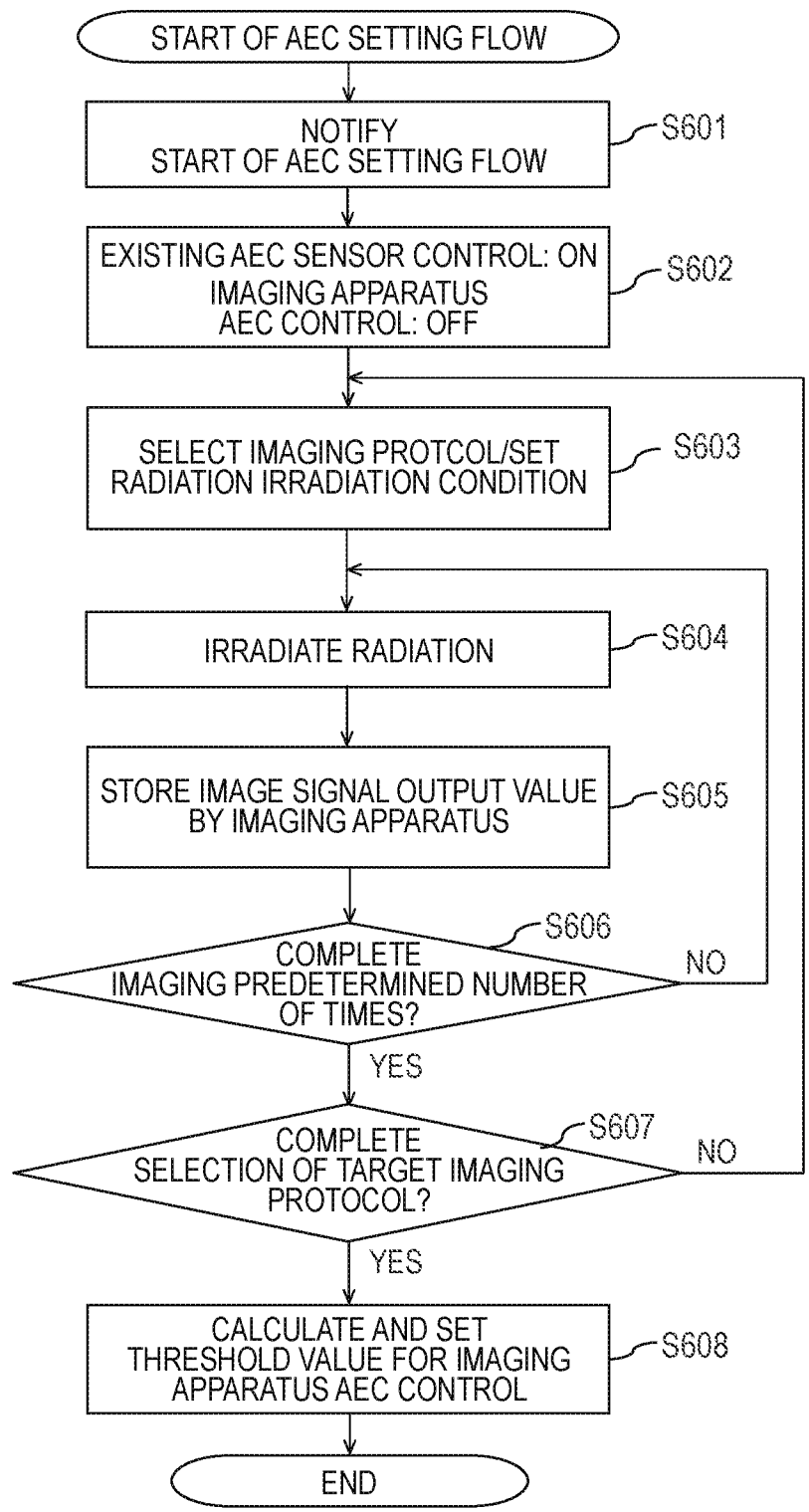

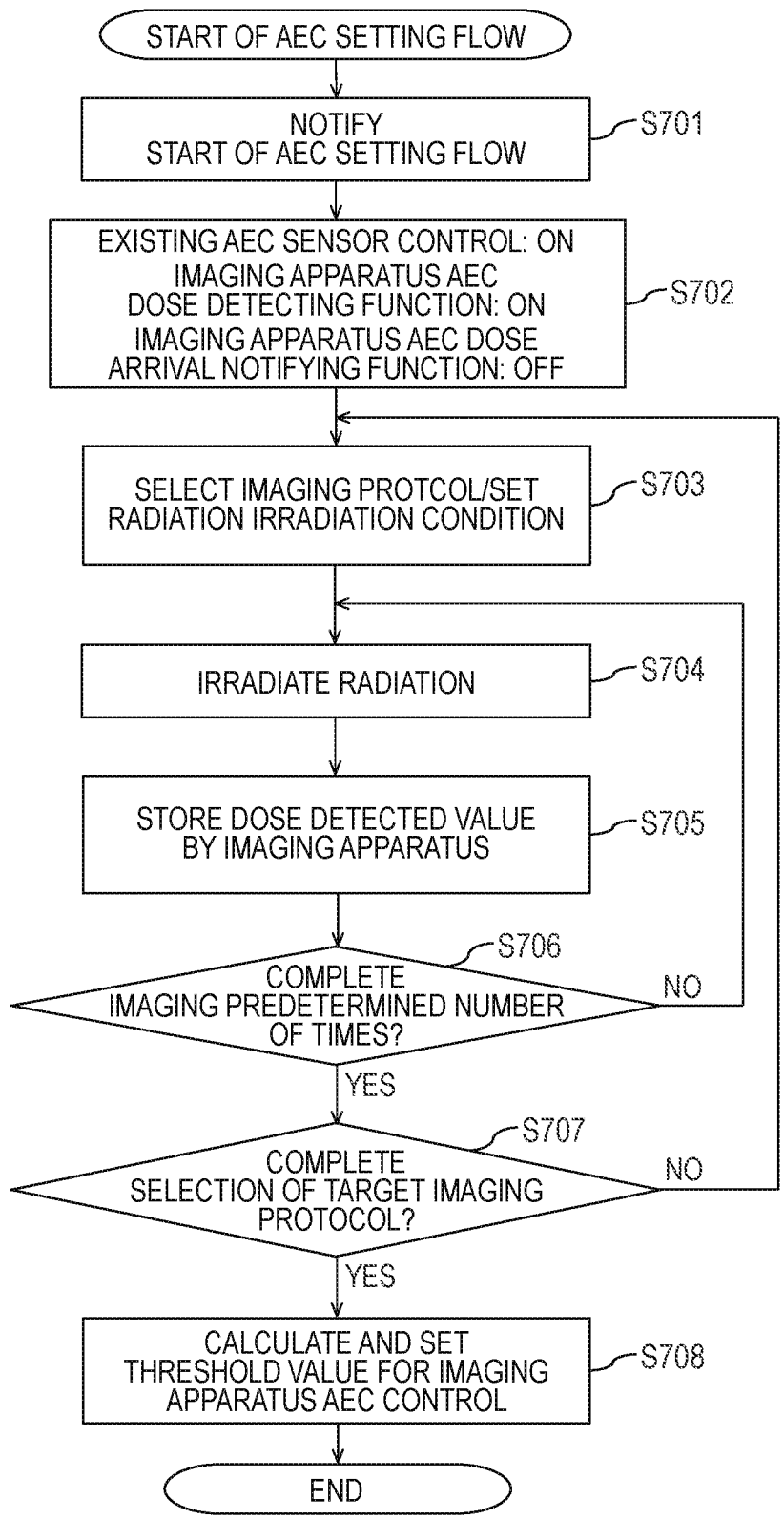

RADIATION IMAGING APPARATUS, RADIATION IMAGING SYSTEM AND CONTROL METHOD OF RADIATION IMAGING APPARATUS

BACKGROUND OF THE INVENTION

Field of the Invention

The present invention relates to a radiation imaging apparatus and a radiation imaging system that perform automatic exposure control of radiation, and a control method of the radiation imaging apparatus.

Description of the Related Art

Radiation imaging apparatuses using a radiation detector (for example, a sensor panel) that detects radiation, such as X-ray, as an electric signal are widely used in the fields of industry and medical treatment. In recent years, multi-functionalization of radiation imaging apparatuses has been considered. To incorporate a function of monitoring the irradiation of radiation has been considered as one of them. With this function, for example, the detection of the timing at which irradiation of radiation is started by a radiation generating apparatus, the detection of the timing at which the irradiation of radiation should be stopped, and the detection of the irradiation amount or accumulated irradiation amount of radiation are enabled. Additionally, automatic exposure control (AEC) is also enabled by detecting the accumulated irradiation amount of radiation transmitted through a subject, and stopping the irradiation of radiation by the radiation generating apparatus at the time when a detected accumulated irradiation amount reaches an appropriate amount.

Generally, when performing the above-described automatic exposure control by using an FPD (Flat Panel Detector) as a radiation detector, an aspect may be taken in which a plate-like AEC sensor, which is different from the FPD, is sandwiched between the subject and the FPD. Here, the AEC sensor measures the dose (irradiation amount) of radiation transmitted through the subject in regions of interest (ROI), which are about 1 to 5 predetermined radiation detecting regions for which the irradiated radiation is to be monitored, and performs the irradiation stop control of radiation when a predetermined dose, which is a threshold value, is reached.

In the radiation imaging using the separate AEC sensor, since it is difficult to carry the FPD and the AEC sensor, the stationary installation type radiation imaging, such as standing position imaging and decubitus imaging, is common.

On the other hand, when an AEC function is mounted inside the FPD, the FPD can be carried as in a conventional FPD, and the radiation imaging using the AEC function is enabled even for postures other than a standing position and a decubitus position. Additionally, also in this case, the radiation imaging using the AEC function is normally performed for the standing position and the decubitus position.

For the above-described AEC, the technology related to an FPD incorporating the AEC function is disclosed in Japanese Patent Application Laid-Open No. 2016-171917. Here, when introducing the FPD incorporating the AEC function into an existing radiation imaging system, some customers desire to take over the conditions of the automatic exposure control by the AEC sensor provided in the existing radiation imaging system.

Japanese Patent No. 5706279 discloses the technology of performing the same AEC as the AEC sensor provided in the existing radiation imaging system.

However, in each of the technologies disclosed in Japanese Patent Application Laid-Open No. 2016-171917 and Japanese Patent No. 5706279, complicated work was required in order to take over parameters of AEC information on the existing radiation imaging system side.

The present invention has been made in view of such problems, and an object is to provide, in a radiation imaging system that performs the automatic exposure control (AEC) of radiation, a mechanism that can reflect the automatic exposure control by an AEC sensor to the automatic exposure control by a radiation detector with high accuracy.

SUMMARY OF THE INVENTION

The radiation imaging apparatus according an aspect of the present invention includes a radiation detector including a pixel array in which a plurality of pixels being capable of detecting radiation as electric signals are arranged, the radiation transmitted through an AEC sensor used for performing automatic exposure control of radiation irradiated from a radiation generating apparatus, a notifying unit configured to perform threshold value reached notification to the radiation generating apparatus, if a dose value of the radiation incident on the pixel array reaches a threshold value, and a threshold value setting unit configured to set the threshold value in second radiation imaging in which automatic exposure control of the radiation by the radiation detector is performed after first radiation imaging in which the automatic exposure control of the radiation by the AEC sensor is performed, based on pixel values related to the electric signals detected by the plurality of pixels in the first radiation imaging.

According an aspect of the present invention, the threshold value setting unit may be configured to set the threshold value in the second radiation imaging based on the pixel values related to the electric signals obtained in the plurality of pixels for each radiation image obtained in the first radiation imaging.

According an aspect of the present invention, the threshold value setting unit may be configured to set the threshold value in the second radiation imaging based on the pixel values related to the electric signals obtained in the plurality of pixels for each predetermined time period shorter than an obtaining time period of a radiation image in the first radiation imaging.

According an aspect of the present invention, a region of interest including a plurality of pixels may be provided in a part of a region of the pixel array, and the threshold value setting unit may be configured to set the threshold value in the second radiation imaging based on pixel values in the plurality of pixels included in the region of interest.

According an aspect of the present invention, a plurality of regions of interest may be provided in the pixel array, and the threshold value setting unit is configured to set the threshold value in the second radiation imaging based on the pixel values in the plurality of pixels included in the plurality of regions of interest.

According an aspect of the present invention, the radiation imaging apparatus may further include an on/off setting unit configured to set ON/OFF of the automatic exposure control of the radiation by the radiation detector, wherein the on/off setting unit is configured to set the automatic exposure control of the radiation by the radiation detector to OFF when the first radiation imaging is performed.

According an aspect of the present invention, when setting the automatic exposure control of the radiation by the radiation detector to OFF, the on/off setting unit may be configured to perform at least one setting of turning OFF a dose value detecting function of the radiation based on the pixel values in the plurality of pixels, and turning OFF a threshold value reached notifying function by the notifying unit based on the dose value detecting function.

According an aspect of the present invention, the on/off setting unit may be configured to independently set turning OFF the dose value detecting function and turning OFF the threshold value reached notifying function.

According an aspect of the present invention, the on/off setting unit may be configured to set the dose value detecting function to ON and set the threshold value reached notifying function to OFF when the first radiation imaging is performed.

According an aspect of the present invention, the threshold value in the second radiation imaging may be switchable between a threshold value based on the pixel values related to the electric signals obtained in the plurality of pixels, and a threshold value held in the radiation imaging apparatus comprising the radiation detector, based on one of an instruction by an operator and subject information related to the subject.

According an aspect of the present invention, the pixel array may include a plurality of first pixels configured to detect the radiation as electric signals, and a plurality of second pixels configured to detect the radiation as electric signals with a sensitivity different from a sensitivity of the plurality of first pixels.

According an aspect of the present invention, the pixel values may include an accumulated value of the electric signals detected by the plurality of pixels.

According an aspect of the present invention, the threshold value setting unit may be configured to set the threshold value in the second radiation imaging based on the pixel values related to the electric signals in the plurality of pixels when irradiation of the radiation by the radiation generating apparatus is stopped in the first radiation imaging.

The present invention includes a radiation imaging system including the radiation imaging apparatus, and a controlling apparatus connected with the radiation imaging apparatus and the radiation generating apparatus and configured to control the radiation imaging apparatus and the radiation generating apparatus.

Additionally, the present invention includes a control method of the above-described radiation imaging apparatus.

Further features of the present invention will become apparent from the following description of exemplary embodiments with reference to the attached drawings.

BRIEF DESCRIPTION OF THE DRAWINGS

FIG. 6 is a flowchart for illustrating an example of the processing procedure in a control method of the radiation imaging system according to the first embodiment of the present invention.

FIG. 7 is a flowchart for illustrating an example of the processing procedure in a control method of the radiation imaging system according to a second embodiment of the present invention.

DESCRIPTION OF THE EMBODIMENTS

Hereinafter, referring to drawings, modes (embodiments) for implementing the present invention will be described. Note that, in the embodiments of the present invention set forth below, although an example will be described that assumes a case where an X-ray is applied as radiation in the present invention, the radiation to be applied is not limited to an X-ray in the present invention, and other radiation, such as an alpha ray, a beta ray and a gamma ray, can also be applied.

First Embodiment

First, a first embodiment of the present invention will be described.

Figure 1:
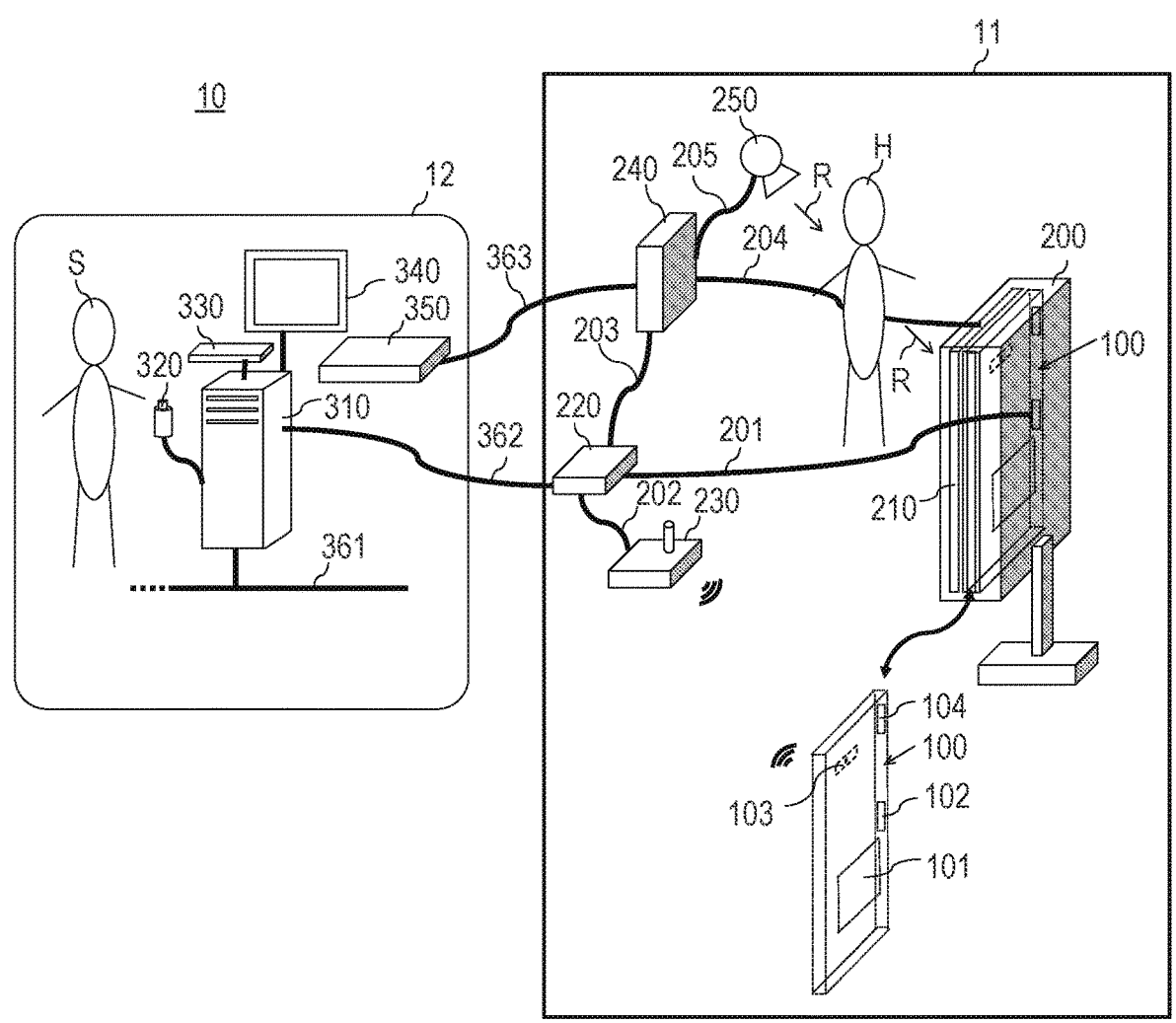
FIG. 1 is a diagram for illustrating an example of the schematic configuration of a radiation imaging system according to a first embodiment of the present invention.

FIG. 1 is a diagram for illustrating an example of the schematic configuration of a radiation imaging system 10 according to the first embodiment of the present invention. As illustrated in FIG. 1, the radiation imaging system 10 is configured in a radiation room 11 and a control room 12. The radiation room 11 is a room where the irradiation of radiation R to a subject H, who is a subject, and the radiation imaging of the subject H are performed. The control room 12 is a room located in the vicinity of the radiation room 11, and for controlling the radiation imaging of the subject H in the radiation room 11 by an operator S.

The radiation room 11 includes, as one configuration of the radiation imaging system 10, a radiation imaging apparatus 100, a standing position stand 200, communication cables 201 to 205, an AEC sensor 210, a communication controlling apparatus 220, an access point 230, a radiation generating apparatus 240, and a radiation source 250. Additionally, the control room 12 includes, as one configuration of the radiation imaging system 10, a controlling apparatus 310, a radiation irradiation switch 320, an input apparatus 330, a display apparatus 340, a console 350, an intra-hospital LAN 361, and communication cables 362 and 363.

First, in the radiation imaging system 10 illustrated in FIG. 1, the configuration units configured in the radiation room 11 will be described.

The radiation imaging apparatus 100 is an apparatus that detects the radiation R transmitted through the subject H as an electric signal, and images a radiation image of the subject H. Additionally, in the first embodiment, the radiation imaging apparatus 100 is assumed to be an apparatus having the above-described function of automatic exposure control (AEC). As illustrated in FIG. 1, this radiation imaging apparatus 100 includes a power supply controlling unit 101, a wired communication unit 102, a wireless communication unit 103, and an attachment detecting unit 104.

The power supply controlling unit 101 is a configuration unit that includes a battery, etc. The wired communication unit 102 communicates information with cable connection using, for example, a communication standard having a predetermined agreement, or a standard such as Ethernet (registered trademark). The wireless communication unit 103 includes, for example, an antenna and a circuit board provided with a communication IC, and the circuit board performs wireless communication processing with a wireless LAN-based protocol via the antenna. Note that the frequency band, standard, and system of the wireless communication in the wireless communication unit 103 are not limited, and short-range radio such as NFC and Bluetooth (registered trademark), and a system such as UWB may be used. Additionally, the wireless communication unit 103 may include a plurality of wireless communication systems, and perform communication by appropriately selecting them. The attachment detecting unit 104 is a configuration unit which detects that the radiation imaging apparatus 100 is attached to the standing position stand 200.

The standing position stand 200 is a stand (gantry) that allows radiation imaging in a standing position when the radiation imaging apparatus 100 is attached. The radiation imaging apparatus 100 can be attached to and detached from this standing position stand 200, and can perform imaging whether attached or detached The communication cable 201 is a cable for communicatively connecting the radiation imaging apparatus 100 to the communication controlling apparatus 220. The communication cable 202 is a cable for communicatively connecting the access point (AP) 230 to the communication controlling apparatus 220. The communication cable 203 is a cable for communicatively connecting the radiation generating apparatus 240 to the communication controlling apparatus 220. The communication cable 204 is a cable for communicatively connecting the radiation generating apparatus 240 to the AEC sensor 210. The communication cable 205 is a cable for communicatively connecting the radiation source 250 to the radiation generating apparatus 240.

The AEC sensor 210 is a plate-like sensor for performing automatic exposure control (AEC) of the radiation R. When performing radiation imaging in a state where the radiation imaging apparatus 100 is attached to the standing position stand 200, this AEC sensor 210 is arranged to be located between the radiation source 250 (and further, the subject H) and the radiation imaging apparatus 100. In automatic exposure control (AEC) of the radiation R by an existing AEC sensor 210, for example, an analog signal related to the dose of the radiation R detected in a radiation detecting unit, such as an ion chamber and a photo timer, is output to the radiation generating apparatus 240 via the communication cable 204. Then, in an internal exposure controlling unit in the radiation generating apparatus 240, when the accumulated value of the analog signal from the AEC sensor 210 reaches a predetermined threshold value, automatic exposure control (AEC) is performed by stopping the irradiation of the radiation R from the radiation source 250.

The communication controlling apparatus 220 is a configuration unit that controls communication in each configuration unit of the radiation imaging system 10. Specifically, the communication controlling apparatus 220 controls the communication in each configuration unit so that, for example, the access point 230, the radiation generating apparatus 240, and the controlling apparatus 310 can communicate with each other.

The access point 230 performs wireless communication with the radiation imaging apparatus 100. For example, when the radiation imaging apparatus 100 is detached from the standing position stand 200 and used, the access point 230 is used for relaying communication among the radiation imaging apparatus 100, the controlling apparatus 310, and the radiation generating apparatus 240. Note that one of the radiation imaging apparatus 100 and the communication controlling apparatus 220 may have the function of the access point. In that case, the radiation imaging apparatus 100, the controlling apparatus 310, and the radiation generating apparatus 240 may perform communication not via the access point 230, but via the access point of one of the radiation imaging apparatus 100 and the communication controlling apparatus 220.

The radiation generating apparatus 240 is an apparatus that generates the radiation R from the radiation source 250 toward the subject H, who is a subject body. Specifically, the radiation generating apparatus 240 controls the radiation source 250 via the communication cable 205 so as to irradiate the radiation R based on a predetermined irradiation condition. The radiation source 250 is a configuration unit that irradiates the radiation R to the subject H, according to the control by the radiation generating apparatus 240.

Subsequently, the configuration units configured in the control room 12 in the radiation imaging system 10 illustrated in FIG. 1 will be described.

The controlling apparatus 310 communicates with the radiation generating apparatus 240 and the radiation imaging apparatus 100 via the communication cable 362 and the communication controlling apparatus 220, and comprehensively controls the radiation imaging system 10.

The radiation irradiation switch 320 is a switch for inputting the timing of irradiation of the radiation R from the radiation source 250 by an operation by the operator S.

The input apparatus 330 is an apparatus for inputting an instruction from the operator S to the controlling apparatus 310, and includes, for example, various input devices such as a keyboard and a touch panel.

The display apparatus 340 is an apparatus that displays a radiation image subjected to image processing and a GUI, and includes a display.

The console 350 is an apparatus for the operator S to set various kinds of conditions to the radiation generating apparatus 240, and is communicatively connected to the radiation generating apparatus 240 via the communication cable 363.

The intra-hospital LAN 361 is a backbone network in a hospital. The communication cable 362 is a cable for communicatively connecting the controlling apparatus 310 to the communication controlling apparatus 220 in the radiation room 11. The communication cable 363 is a cable for communicatively connecting the console 350 to the radiation generating apparatus 240 in the radiation room 11.

Figure 2:
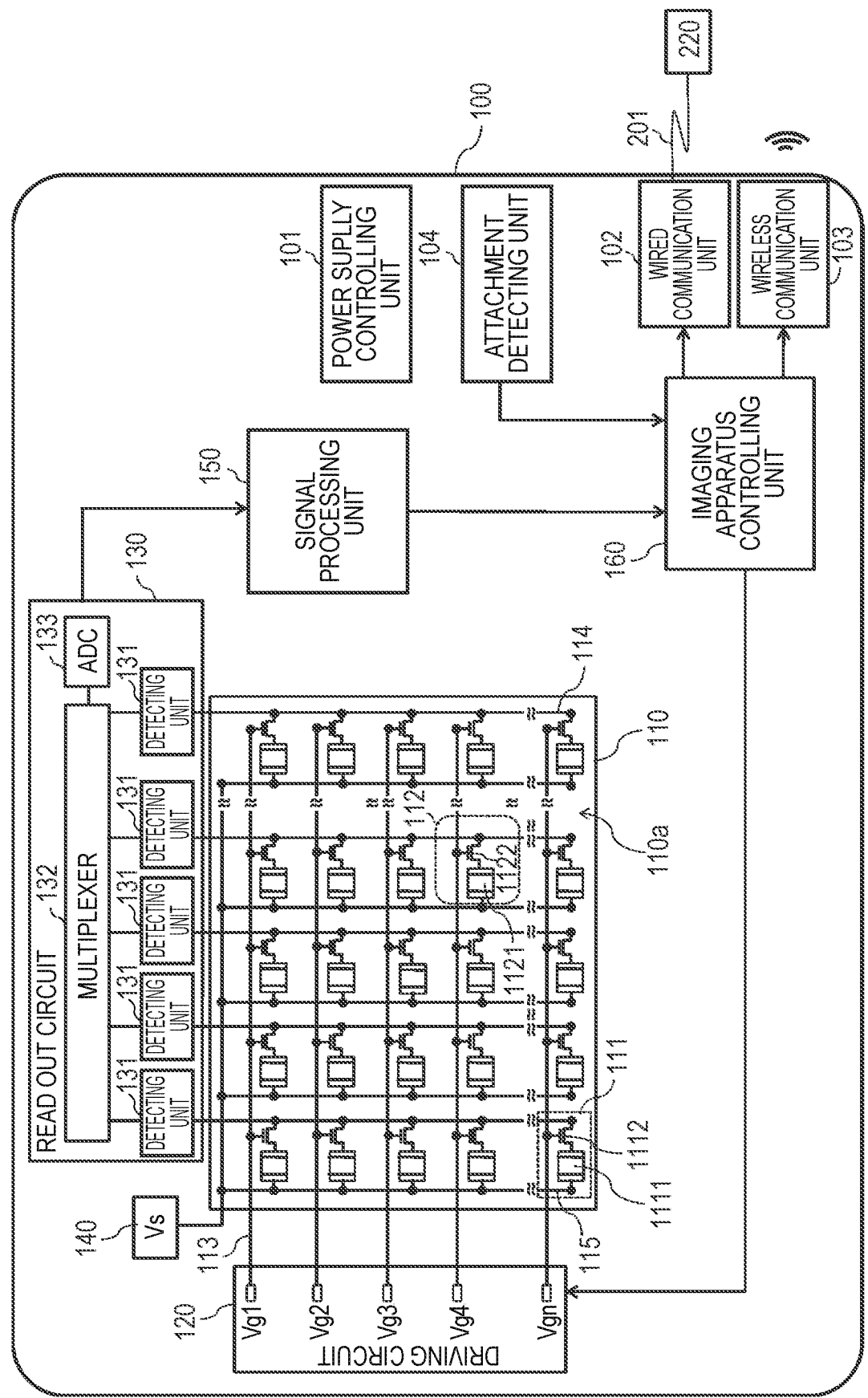
FIG. 2 is a diagram for illustrating an example of the internal configuration of a radiation imaging apparatus illustrated in FIG. 1.

Next, the internal configuration of the radiation imaging apparatus 100 illustrated in FIG. 1 will be described. FIG. 2 is a diagram for illustrating an example of the internal configuration of the radiation imaging apparatus 100 illustrated in FIG. 1. In this FIG. 2, the same numerals are given to the configurations similar to the configurations illustrated in FIG. 1, and a detailed description thereof is omitted.

As described above using FIG. 1, the radiation imaging apparatus 100 includes the power supply controlling unit 101, the wired communication unit 102, the wireless communication unit 103, and the attachment detecting unit 104. Further, as illustrated in FIG. 2, the radiation imaging apparatus 100 includes a radiation detector 110, a driving circuit 120, a read out circuit 130, a power supply circuit 140, a signal processing unit 150, and an imaging apparatus controlling unit 160.

The radiation detector 110 includes a pixel array 110a which is an imaging region where a plurality of pixels for detecting the incident radiation R as electric signals are arranged, and is a configuration unit that outputs the electric signals related to a radiation image. Specifically, the plurality of pixels arranged in a matrix are arranged in the pixel array 110a. The plurality of pixels arranged in the pixel array 110a include a plurality of detection pixels 111 and a plurality of correction pixels 112, and each of which convert the incident radiation R into electric signals. Here, the detection pixel 111 is an imaging pixel that outputs an electric signal for obtaining a radiation image or obtaining the dose of the incident radiation R (the irradiation amount of the incident radiation R). The correction pixel 112 is a pixel that outputs an electric signal for removing a dark current component and a crosstalk component.

Each of the plurality of detection pixels 111 is a first pixel including a first conversion element 1111 and a first switching element 1112. The first conversion element 1111 is an element that converts the incident radiation R into an electric signal. This first conversion element 1111 includes, for example, a scintillator that converts the incident radiation R into light, and a photoelectric conversion element that converts the light generated by the scintillator into an electric signal, and converts the incident radiation R into an electric signal. In this case, the scintillator is formed into a sheet shape so as to cover the pixel array 110a, which is the imaging region, and is shared by a plurality of pixels. Note that the first conversion element 1111 may convert the incident radiation R into the electric signal by including a conversion element that directly converts the incident radiation R to the electric signal, without including the above-described scintillator. The first switching element 1112 is an element for electrically connecting a column signal line 114 to the first conversion element 1111, and outputs an electric signal obtained in the first conversion element 1111 to the column signal line 114. This first switching element 1112 includes, for example, a thin film transistor (TFT) in which an active region is formed by a semiconductor such as an amorphous silicon or a polycrystalline silicon (preferably, a polycrystalline silicon).

Each of the plurality of correction pixels 112 is a second pixel that includes a second conversion element 1121 and a second switching element 1122. The second conversion element 1121 is formed with the same configuration as the first conversion element 1111, and converts the incident radiation R into an electric signal. The second switching element 1122 is formed with the same configuration as the first switching element 1112, is a switch for electrically connecting the column signal line 114 to the second conversion element 1121, and outputs the electric signal obtained in the second conversion element 1121 to the column signal line 114. Here, although each of the plurality of correction pixels 112 has basically the same configuration as each of the above-described plurality of detection pixels 111, in order to output a different electric signal for the incident radiation R, the radiation R is detected as an electric signal with a sensitivity different from that in the detection pixel 111. Specifically, in the first embodiment, each of the plurality of correction pixels 112 detects the radiation R as the electric signal with a lower sensitivity than each of the plurality of detection pixels 111. In other words, in the first embodiment, each of the plurality of detection pixels 111 detects the radiation R as an electric signal with a higher sensitivity than each of the plurality of correction pixels 112. The sensitivity with respect to the radiation R is made higher for the detection pixel 111 than for the correction pixel 112 by, for example, making a region for detecting the radiation R larger for the detection pixel 111 than for the correction pixel 112. On this occasion, for example, a mode in which the region for detecting the radiation R is made larger for the detection pixel 111 than for the correction pixel 112 can be taken by arranging a shielding member that shields radiation or light in at least a part of the region of the second conversion element 1121 of the correction pixel 112. For example, in a case of a direct-type second conversion element 1121 that directly converts the incident radiation R to an electric signal, a mode of providing a shielding member using a heavy metal, such as a lead, on the second conversion element 1121 as the shielding member that shields the radiation R can be taken. Additionally, for example, in a case of an indirect-type second conversion element 1121 that converts the incident radiation R into light by the scintillator, and converts this light into an electric signal by a photoelectric conversion element, a shielding film of, for example, aluminum may be provided between the scintillator and the photoelectric conversion element as the shielding member that shields light. In this manner, whether the second conversion element 1121 is of the direct type or the indirect-type, the correction pixel 112 is arranged in a region where the shielding member overlaps with at least a part of the second conversion element 1121 of the correction pixel 112 in a plan view with respect to the pixel array 110a which is the imaging region. Accordingly, in the first embodiment, the information indicating the dose value of the radiation R (the irradiation amount value of the radiation R) obtained by using the detection pixel 111 can be more correctly generated by subtraction of the electric signal obtained from the detection pixel 111, and the electric signal obtained from the correction pixel 112.

Figure 3:
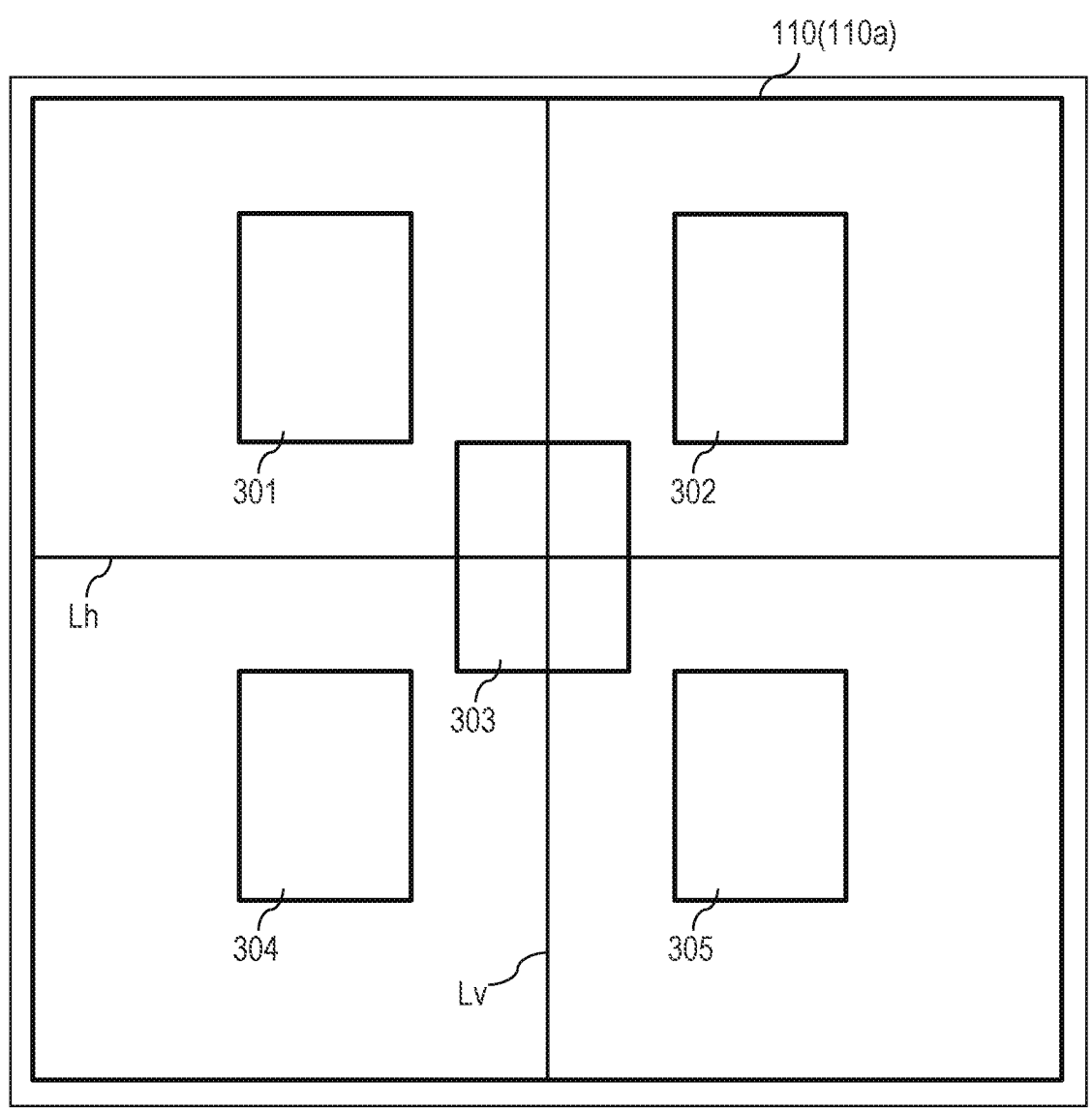
FIG. 3 is a diagram for illustrating an arrangement example of a plurality of regions of interest (ROI) that are set in a pixel array which is an imaging region of a radiation detector illustrated in FIG. 2.

FIG. 3 is a diagram for illustrating an arrangement example of a plurality of regions of interest (ROI) 301 to 305 that are set in the pixel array 110a which is the imaging region of the radiation detector 110 illustrated in FIG. 2. Additionally, FIG. 3 also illustrates, for example, a center line Lh parallel to a drive line 113, and a center line Lv perpendicular to the drive line 113 in the pixel array 110a which is the imaging region. In the first embodiment, the regions of interest (ROI) 301 to 305 are assumed to be regions for detecting the dose of the radiation R that is incident on the pixel array 110a, in order to perform automatic exposure control (AEC) related to stopping the irradiation of the radiation R from the radiation source 250. That is, in the first embodiment, similar to the AEC sensor 210, the radiation detector 110 includes the AEC function. Note that, in the first embodiment, the AEC sensor 210 can also take a mode in which regions of interest (ROI) similar to the regions of interest (ROI) 301 to 305 of the radiation detector 110 illustrated in FIG. 3 are set. Additionally, in the first embodiment, it is assumed that, in the pixel array 110a of the radiation detector 110, the detection pixel 111 and the correction pixel 112 are arranged in the regions of interest (ROI) 301 to 305.

Here, let us return to the description of FIG. 2 again. The radiation detector 110 includes a plurality of column signal lines 114, a plurality of drive lines 113, and a plurality of bias lines 115 in the region of the pixel array 110a. The plurality of column signal lines 114 are connected in common to the pixels of the respective columns in the pixel array 110a. The plurality of drive lines 113 are connected in common to the pixels of the respective rows in the pixel array 110a. The plurality of bias lines 115 are connected in common to the pixels of the respective columns in the pixel array 110a.

In the pixel array 110a, first electrodes of the first conversion element 1111 and the second conversion element 1121 are connected to first main electrodes of the first switching element 1112 and the second switching element 1122, respectively. Additionally, second electrodes of the first conversion element 1111 and the second conversion element 1121 are connected to the bias lines 115. Here, one bias line 115 extends in the column direction of the pixel array 110a, and is connected in common to the second electrodes of the plurality of first conversion elements 1111 and second conversion elements 1121 arranged in the column direction. Additionally, the second main electrodes of the first switching element 1112 and the second switching element 1122 are connected to the column signal lines 114.

In this manner, the second main electrodes of the first switching element 1112 and the second switching element 1122 of respective columns are connected to the column signal lines 114 of the respective columns. Additionally, control electrodes of the first switching element 1112 and the second switching element 1122 of respective rows are connected to the drive lines 113 of the respective rows. In addition, the plurality of column signal lines 114 are connected to the read out circuit 130.

The driving circuit 120 supplies voltages Vg1 to Vgn related to driving of pixels to the plurality of pixels via the plurality of drive lines 113 on a line by line basis.

The power supply circuit 140 supplies a bias voltage Vs to the bias lines 115. The power supply controlling unit 101 includes a battery, a DC-DC converter and so on. The power supply controlling unit 101 controls the power supply circuit 140, and generates an analog circuit power supply voltage, and a digital circuit power supply voltage for performing driving control, communication, and so on.

The read out circuit 130 includes a plurality of detecting units 131, a multiplexer 132, and an analog-to-digital converter (hereinafter referred to as "the AD converter") 133. As illustrated in FIG. 2, each of the plurality of column signal lines 114 is connected to the corresponding detecting unit 131 of the plurality of detecting units 131. On this occasion, one column signal line 114 is connected to one detecting unit 131. The detecting unit 131 includes, for example, a differential amplifier, and amplifies the electric signal of the column signal line 114. The multiplexer 132 selects the plurality of detecting units 131 in a predetermined order, and supplies the electric signal from the selected detecting unit 131 to the AD converter 133. The AD converter 133 converts the supplied electric signal from an analog signal into a digital signal, and outputs the digital signal.

The signal processing unit 150 processes the output signal of the read out circuit 130 (the AD converter 133), and outputs the information indicating the dose value of the radiation R (the irradiation amount value of the radiation R) for the regions of interest (ROI) 301 to 305 of the radiation imaging apparatus 100. On this occasion, the signal processing unit 150 performs, for example, characteristic correction processing for removing the dark current component and the crosstalk component of the radiation imaging apparatus 100 using the correction pixels 112, the irradiation detection of the radiation, and the computation of the irradiation amount and accumulated irradiation amount of the radiation.

Further, the signal processing unit 150 processes the output signal of the read out circuit 130 (the AD converter 133) to output the information indicating a radiation image of the subject H, who is the subject body. On this occasion, the signal processing unit 150 performs, for example, signal processing for subtracting the electric signal related to the dark current component or the crosstalk component generated by the correction pixels 112 from the electric signal related to the radiation image generated by the detection pixels 111.

The imaging apparatus controlling unit 160 controls the driving circuit 120, the read out circuit 130, and so on, based on the information from the signal processing unit 150 and a control command from the controlling apparatus 310 illustrated in FIG. 1. Further, the imaging apparatus controlling unit 160 transmits the information from the signal processing unit 150 to the communication controlling apparatus 220 and the controlling apparatus 310 via one of the wired communication unit 102 and the wireless communication unit 103.

Figure 4:
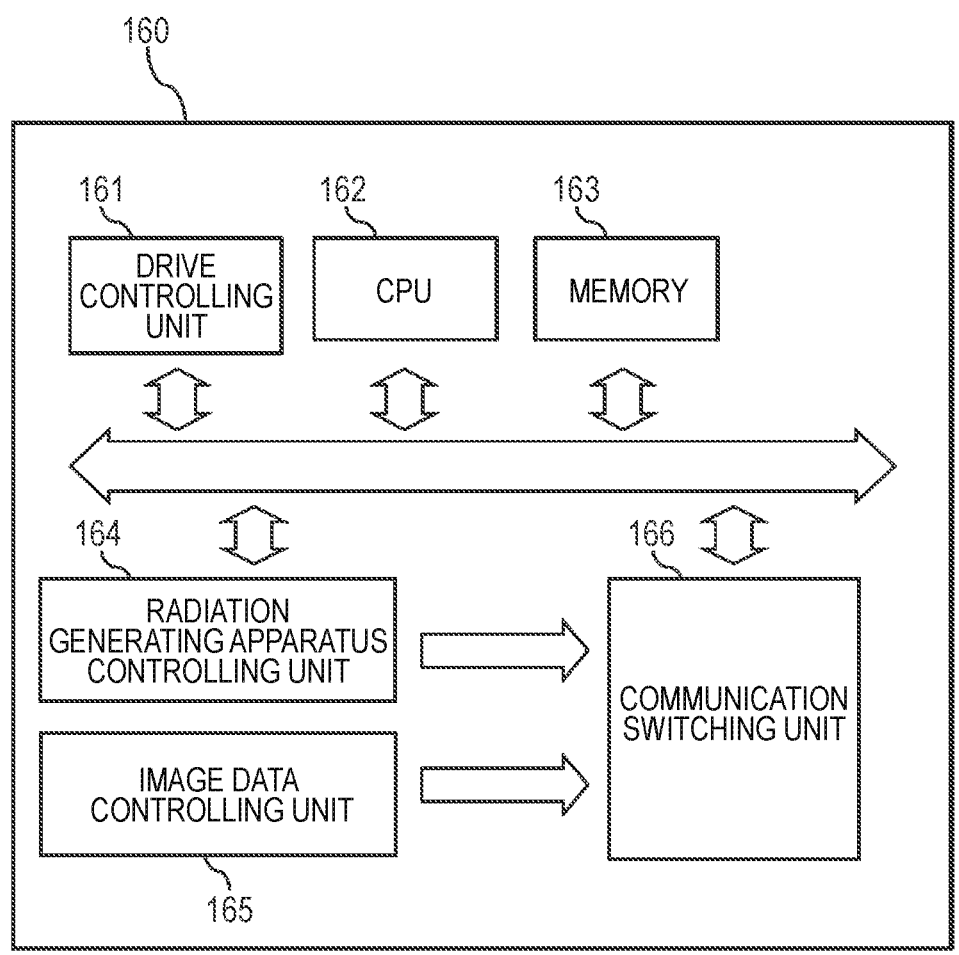
FIG. 4 is a diagram for illustrating an example of the internal configuration of an imaging apparatus controlling unit illustrated in FIG. 2.

FIG. 4 is a diagram for illustrating an example of the internal configuration of the imaging apparatus controlling unit 160 illustrated in FIG. 2. As illustrated in FIG. 4, the imaging apparatus controlling unit 160 includes a drive controlling unit 161, a CPU 162, a memory 163, a radiation generating apparatus controlling unit 164, an image data controlling unit 165, and a communication switching unit 166.

The drive controlling unit 161 controls the driving of the driving circuit 120 and the read out circuit 130 illustrated in FIG. 2, based on the information from the signal processing unit 150 illustrated in FIG. 2, and the command from the controlling apparatus 310 illustrated in FIG. 1.

The CPU 162 performs controlling of the entire radiation imaging apparatus 100 by using a program and various kinds of data stored in the memory 163, and performs various kinds of processing.

The memory 163 stores, for example, the program and various kinds of data that are used by the CPU 162 when performing various kinds of control and various kinds of processing. On this occasion, the various kinds of data includes various kinds of data obtained from the processing by the CPU 162, the information indicating a radiation image (radiation image data), the information indicating the dose value of the radiation R (the irradiation amount value of the radiation R), which is radiation irradiation information, a threshold value used for radiation irradiation stop determination in the AEC and so on.

The radiation generating apparatus controlling unit 164 controls the operation of the radiation generating apparatus 240 illustrated in FIG. 1, based on the information from the signal processing unit 150 illustrated in FIG. 2, and the information from the drive controlling unit 161. The radiation generating apparatus controlling unit 164 and the radiation generating apparatus 240 exchange the information on the controlling of the radiation generating apparatus 240 (for example, notifications related to the irradiation start and irradiation stop of the radiation R, and the information indicating the dose value of the radiation R (the irradiation amount value of the radiation R)). Here, it is assumed that the notification from the radiation generating apparatus controlling unit 164 to the radiation generating apparatus 240 includes, as the notification related to the irradiation stop of the radiation R, a threshold value reached notification indicating that the dose value of the radiation R (the irradiation amount value of the radiation R) has reached the threshold value. Then, the radiation generating apparatus controlling unit 164 of the radiation imaging apparatus 100 performing this threshold value reached notification configures a "notifying unit".

Here, in the first embodiment, it is assumed that the radiation imaging in which automatic exposure control (AEC) by the AEC sensor 210 is performed is "first radiation imaging", and the radiation imaging in which automatic exposure control by the AEC function of the radiation detector 110 is performed is "second radiation imaging."

The image data controlling unit 165 performs the control of storing, in the memory 163, the information indicating a radiation image from the signal processing unit 150 illustrated in FIG. 2 as the radiation image data. Additionally, the image data controlling unit 165 controls the communication with the controlling apparatus 310 illustrated in FIG. 1, and exchanges the information indicating a radiation image (the radiation image data) and the information on control (for example, the control command).

The communication switching unit 166 enables the communication by the wired communication unit 102 when the communication cable 201 is connected to the radiation imaging apparatus 100, and enables the communication by the wireless communication unit 103 when the communication cable 201 is removed from the radiation imaging apparatus 100.

Next, the operation of the radiation imaging system 10 at the time of the radiation imaging (the second radiation imaging) for which automatic exposure control (AEC) of the radiation R by the radiation detector 110 of the radiation imaging apparatus 100 is performed will be described.

In FIG. 1, the operator S uses the input apparatus 330 to set subject information such as the ID, name, and date of birth of the subject H, and imaging information such as an imaging site of the subject H to the controlling apparatus 310. On this occasion, for the subject information and the imaging information, in addition to the method in which the operator S performs the setting by direct input to the input apparatus 330, a method can also be applied that automatically performs the setting by selecting, for example, an examination order received via the intra-hospital LAN 361. Additionally, the imaging information can also be set by selecting an imaging protocol that is set in advance.

Subsequently, the operator S uses the input apparatus 330 to input, to the controlling apparatus 310, the dose and the maximum irradiation time of the radiation R, the tube current and tube voltage of the radiation source 250, the region of interest (ROI) for which the dose of the radiation R is detected for performing automatic exposure control (AEC), site information, and so on.

Then, the controlling apparatus 310 transmits the irradiation condition of the radiation R, the region of interest (ROI), the site information, and so on that are input from the input apparatus 330 to the radiation imaging apparatus 100 and the radiation generating apparatus 240. Here, the ROI setting is established when the operator S uses the input apparatus 330 to appropriately select one or more of selectable regions of interest (ROI) (for example, the regions of interest (ROI) 301 to 305 illustrated in FIG. 3) as necessary, which are displayed on the display apparatus 340.

When imaging preparation is completed, subsequently, the operator S presses down the radiation irradiation switch 320. When the radiation irradiation switch 320 is pressed down, the radiation source 250 irradiates the radiation R toward the subject H in accordance with the control by the radiation generating apparatus 240. In that case, the radiation imaging apparatus 100 communicates with the radiation generating apparatus 240, and performs irradiation start control of the radiation R. The radiation R irradiated to the subject H is transmitted through the subject H, and is incident on the radiation imaging apparatus 100 (specifically, the radiation detector 110). The radiation imaging apparatus 100 detects the radiation R incident on the set region of interest (ROI) by the detection pixels 111, and the signal processing unit 150 calculates the accumulated value of the dose (arrived dose) of the radiation R detected in a certain time period by computation as the dose value of the radiation R. Then, the signal processing unit 150 outputs the information indicating the calculated dose value of the radiation R to the imaging apparatus controlling unit 160.

Then, the imaging apparatus controlling unit 160 determines whether or not the dose value of the radiation R, which is the information output from the signal processing unit 150, has reached a threshold value used for the radiation irradiation stop determination, which is held in the memory. On this occasion, the threshold value held in the memory may be set according to, for example, a proper dose defined from the site information and the imaging condition that are input by the operator S. Then, when the dose value of the radiation obtained by the signal processing unit 150 has reached the threshold value held in the memory, the radiation generating apparatus controlling unit 164 performs the threshold value reached notification to the radiation generating apparatus 240 via the communication controlling apparatus 220, etc. In this case, the radiation generating apparatus 240 stops the irradiation of the radiation R from the radiation source 250, based on the timing at which the threshold value reached notification is received from the radiation generating apparatus controlling unit 164. Note that, here, although the example has been described in which the threshold value reached notification is performed from the radiation generating apparatus controlling unit 164 of the radiation imaging apparatus 100, the first embodiment is not limited to this aspect. For example, the dose value of the radiation R for each certain time period may be transmitted from the radiation generating apparatus controlling unit 164 to the radiation generating apparatus 240, and when the radiation generating apparatus 240 determines that the received dose value of the radiation R has reached the threshold value, the irradiation stop of the radiation R may be performed. Further, for example, the dose (arrived dose) of the radiation R for each certain time period may be transmitted from the radiation generating apparatus controlling unit 164 to the radiation generating apparatus 240, and the radiation generating apparatus 240 may calculate the dose value of the radiation R by accumulating the dose of the radiation R, and also perform the subsequent processing.

After the irradiation stop of the radiation R, the radiation detector 110 detects the incident radiation R as electric signals related to a radiation image (radiation image signal). On this occasion, the radiation imaging apparatus 100 drives each pixel of the radiation detector 110 by the driving circuit 120, and reads out the radiation image signal to the read out circuit 130. In the read out circuit 130, an analog radiation image signal is converted into a digital radiation image signal by the AD converter 133. Then, the signal processing unit 150 subtracts, for example, the electric signal related to one of the dark current component and the crosstalk component generated by the correction pixels 112 from the radiation image signal generated by the detection pixels 111, and obtains the information (radiation image data) indicating a proper radiation image. Then, the obtained radiation image data is transferred from the radiation imaging apparatus 100 to the controlling apparatus 310 via the communication controlling apparatus 220, etc.

The controlling apparatus 310 performs image processing of the radiation image data received from the radiation imaging apparatus 100. Then, the controlling apparatus 310 displays, on the display apparatus 340, a radiation image based on the radiation image data subjected to the image processing. In the first embodiment, the controlling apparatus 310 also functions as an image processing apparatus and a display controlling apparatus.

Figure 5:
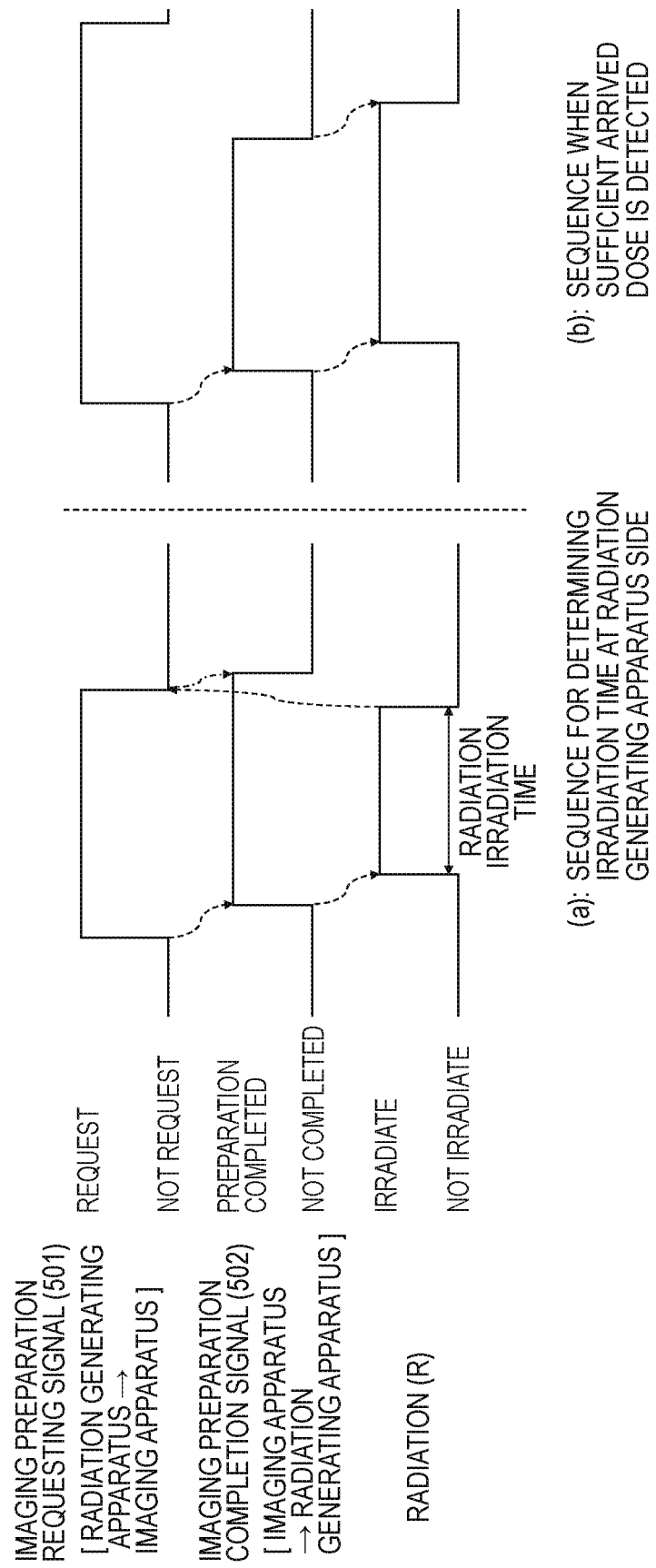
FIG. 5 is a timing chart for illustrating an example of the timing of communication between a radiation generating apparatus and the radiation imaging apparatus illustrated in FIG. 1.

FIG. 5 is a timing chart for illustrating an example of the timing of communication between the radiation generating apparatus 240 and the radiation imaging apparatus 100 illustrated in FIG. 1. Specifically, FIG. 5 illustrates the timing chart in a case of performing handshake communication between the radiation generating apparatus 240 and the radiation imaging apparatus 100. On this occasion, a handshaking signal related to the imaging preparation between the radiation generating apparatus 240 and the radiation imaging apparatus 100 utilizes one of an exclusive digital communication path and its equivalent path. Hereinafter, using FIG. 5, the details of the handshake communication at the time of radiation imaging will be described.

First, using (a) in FIG. 5 illustrated on the left side of FIG. 5, a sequence for determining the irradiation time of the radiation R by the radiation generating apparatus 240 side will be described.

In the case illustrated in this (a) in FIG. 5, the radiation generating apparatus 240 performs preparation for generating radiation in accordance with an operation of the radiation irradiation switch 320 by the operator S. At the time when the anode rotation speed of the radiation source 250 is stabilized and the preparation of the other internal circuits is completed, the radiation generating apparatus 240 outputs an imaging preparation requesting signal 501 illustrated in FIG. 5 at a request level. The imaging preparation requesting signal 501 at the output request level is transmitted to the radiation imaging apparatus 100 via the communication controlling apparatus 220. Then, at the time when the imaging preparation is completed, the radiation imaging apparatus 100 outputs an imaging preparation completion signal 502 at a preparation completion level to the radiation generating apparatus 240 via the communication controlling apparatus 220. Then, the radiation generating apparatus 240 monitors the other signal states, and after confirming that all preparations states are ready, irradiates the radiation R from the radiation source 250. Then, the radiation generating apparatus 240 stops the irradiation of the radiation R based on the radiation irradiation time that is set by the operator S, and outputs the imaging preparation requesting signal 501 at a not-request level. According to the imaging preparation requesting signal 501 at the not-request level output from the radiation generating apparatus 240, the radiation imaging apparatus 100 causes the imaging preparation completion signal 502 to transit to a not-completed state.

Subsequently, using (b) in FIG. 5 illustrated on the right side of FIG. 5, a sequence in a case where a sufficient arrived dose is detected will be described.

The sequence illustrated in (b) in FIG. 5 is the same as the sequence illustrated in (a) in FIG. 5, until the radiation R is irradiated. Thereafter, in the sequence illustrated in (b) in FIG. 5, when a sufficient arrived dose of the radiation R is detected in the inside of the radiation imaging apparatus 100, the radiation imaging apparatus 100 causes the imaging preparation completion signal 502 to transition to a not-completed state, even when the imaging preparation requesting signal 501 is in a request state. Then, the radiation generating apparatus 240 detects that the imaging preparation completion signal 502 has transitioned to the non-completed state, and stops the irradiation of the radiation R from the radiation source 250.

Note that, although the signals are represented in logical circuit signal forms in FIG. 5, as for the imaging preparation requesting signal 501 and the imaging preparation completion signal 502, the communication between the radiation generating apparatus 240 and the radiation imaging apparatus 100 may be realized by command communication. However, in the first embodiment, a signal path capable of transmitting a stop signal in 1 ms or less is desirable, since the signal path is used for exposure control simultaneously with the handshake operation at the time of irradiation of the radiation R, or suppression of the irradiating radiation R when a sufficient dose is reached. In this viewpoint, a mechanical relay, etc. is not desirable, and a photo coupler, a photomos relay, etc. should be employed for a device to be used for an IF signal generating unit. Additionally, also for the command communication, not low speed RS232C and wireless communication or the like that is not reliable for high speed communication, but Ethernet communication that eliminates other devices by using 100BaseTX/1000BaseT or the like with cables, and dedicated communication that can guarantee the delay time are desirable. On the other hand, in a case where only the dose suppression for excessive irradiation of the radiation R that does not contribute to image quality improvement is intended, if the specification is specified such that a stop function may be activated at the time of long time irradiation for, for example, about 1s, the object can be achieved even when there is delay of, for example, about 100 ms. Therefore, the function realization is possible with an interface performing the normal imaging handshake that does not intend the dose suppression, and including the configuration previously listed as the inappropriate example.

FIG. 6 is a flowchart for illustrating an example of the processing procedure in a control method of the radiation imaging system 10 according to the first embodiment of the present invention. Hereinafter, using this FIG. 6, a method will be described that sets an AEC stop condition on the radiation imaging apparatus 100 side, according to an AEC irradiation stop condition that is set in an existing AEC system (that may be configured by the AEC sensor 210 and the radiation generating apparatus 240).

Note that the flowchart illustrated in FIG. 6 is normally implemented by a serviceman, when introducing the AEC function on the new radiation imaging apparatus 100 side into the existing AEC system. First, an AEC setting flow on the radiation imaging apparatus 100 side is selected via the input apparatus 330 by the operator S as the serviceman. This selection of the AEC setting flow is generally provided in a menu for servicemen.

When the AEC setting flow is started, in step S601 of FIG. 6, the controlling apparatus 310 notifies the radiation imaging apparatus 100 that the AEC setting flow is started.

Subsequently, in step S602, for example, the controlling apparatus 310 sets the automatic exposure control (AEC) function of the radiation R by the AEC sensor 210, which is the existing AEC system, to ON. Further, in step S602, for example, the controlling apparatus 310 sets the automatic exposure control (AEC) function of the radiation R by the radiation detector 110 of the radiation imaging apparatus 100 to OFF. For example, the controlling apparatus 310 that sets ON/OFF of the automatic exposure control (AEC) function of the radiation R by this radiation detector 110 and AEC sensor 210 configures an "on/off setting unit".

Here, in the first embodiment, the AEC function includes a dose value detecting function for the automatic exposure control (AEC) of the radiation R, and a threshold value reached notifying function in a case where the dose value of the radiation R detected by the dose value detecting function reaches the threshold value. Then, setting the AEC function to ON is, for example, setting both the dose value detecting function and the threshold value reached notifying function to ON. Additionally, setting the AEC function to OFF is, for example, setting one or both of the dose value detecting function and the threshold value reached notifying function to OFF (that is, at least one of the dose value detecting function and the threshold value reached notifying function is turned OFF). On this occasion, in the first embodiment, for example, the controlling apparatus 310 can independently set turning OFF of the dose value detecting function and turning OFF of the threshold value reached notifying function.

When the setting in step S602 is performed, the processing of radiation imaging (first radiation imaging) in which the automatic exposure control (AEC) by the AEC sensor 210 is performed is started. Specifically, first, in step S603, for example, the controlling apparatus 310 selects an imaging protocol, which is a target of the existing AEC (the automatic exposure control by the AEC sensor 210), based on the information that is input by the operator S via the input apparatus 330. On this occasion, the imaging site information of the subject H is included in the imaging protocol. Then, according to the set imaging protocol, frame rate setting information, sensitivity setting information, and so on are transmitted to the radiation imaging apparatus 100 as an imaging mode. Also, in step S603, for example, the radiation generating apparatus 240 sets the irradiation conditions of the radiation R, based on the information that is input by the operator S via the console 350. On this occasion, the setting of the tube voltage and tube current of the radiation source 250, irradiation time timeout setting and so on are included in the irradiation conditions.

Subsequently, in step S604, the radiation generating apparatus 240 irradiates the radiation R from the radiation source 250, based on the irradiation conditions, etc. that are set in step S603. Thereafter, when the accumulated value of an analog signal from the existing AEC sensor 210 reaches a predetermined threshold value, the radiation generating apparatus 240 stops the irradiation of the radiation R from the radiation source 250.

Subsequently, in step S605, the radiation imaging apparatus 100 stores, in the memory 163, pixel values related to electric signals in the plurality of pixels of the radiation detector 110 at the time when the irradiation of the radiation R by the radiation generating apparatus 240 is stopped. On this occasion, the radiation imaging apparatus 100 stores, in the memory 163, the pixel values related to the electric signals obtained in the plurality of pixels included in one or more regions of interest that are selected from the plurality of regions of interest (ROI) 301 to 305, for each radiation image obtained by the first radiation imaging. Note that the pixel values stored in the memory 163 here correspond to image signal output values in the plurality of pixels included in one or more selected regions of interest.

Subsequently, in step S606, for example, the radiation imaging apparatus 100 determines whether or not a predetermined number of times of radiation imaging is completed. Here, in the first embodiment, the irradiation of the radiation R with the same imaging protocol may be performed a plurality of times. The influence due to variation in each radiation imaging can be reduced by performing the irradiation of the radiation R a plurality of times, and calculating the average value of the image signal output value for each radiation imaging. As a result of this determination in step S606, if the predetermined number of times of radiation imaging is not completed (step S606/NO), the processing returns to step S604, and step S604 and the subsequent processing are performed again.

On the other hand, as the result of the determination in step S606, if the predetermined number of times of radiation imaging is completed (step S606/YES), the processing proceeds to step S607. When the processing proceeds to step S607, for example, the radiation imaging apparatus 100 or the controlling apparatus 310 determines whether or not the selection of the target imaging protocol is completed. This processing in step S607 is for repeating the same processing also for the remaining imaging protocols that require the AEC setting in the radiation imaging apparatus 100. As a result of this determination in step S607, if the selection of the target imaging protocol is not completed (step S607/NO), the processing returns to step S603, and step S603 and the subsequent processing are performed again.

On the other hand, as the result of the determination in step S607, if the selection of the target imaging protocol is completed (step S607/YES), the processing proceeds to step S608. When the processing proceeds to step S608, the radiation imaging apparatus 100 sets the pixel value (image signal output value) in the imaging mode corresponding to each imaging protocol, which is stored in the memory 163 in step S605, as the threshold value in the automatic exposure control of the radiation R by the radiation detector 110. This threshold value set in step S608 is the threshold value used in the second radiation imaging in which the automatic exposure control of the radiation R by the radiation detector 110 is performed after the first radiation imaging in which the automatic exposure control by the AEC sensor 210 is performed. This processing in step S608 is performed in, for example, the configuration unit of the radiation imaging apparatus 100, such as the CPU 162 or the radiation generating apparatus controlling unit 164. Then, the configuration unit (the CPU 162 or the radiation generating apparatus controlling unit 164) of the radiation imaging apparatus 100 that performs this setting of the threshold value in step S608 configures a "threshold value setting unit".

Then, when it proceeds to the second radiation imaging, in a case where the dose value of the radiation R that is incident on the pixel array 110a (the selected region of interest) reaches the threshold value that is set in step S608, the radiation generating apparatus controlling unit 164 performs the threshold value reached notification to the radiation generating apparatus 240. The radiation generating apparatus controlling unit 164 that performs this threshold value reached notification configures a "notifying unit".

When the processing in step S608 is completed, the processing of the flowchart illustrated in FIG. 6 is ended.

By performing the above-described processing, the AEC can also be performed in the AEC function of the newly introduced radiation imaging apparatus 100, under an irradiation dose condition of the radiation R equivalent to that in the automatic exposure control (AEC) by the AEC sensor 210 which is the existing AEC system. Note that, when the AEC setting of the radiation imaging apparatus 100 according to the first embodiment is performed, the AEC according to the arrived dose in the pixel array 110a of the radiation imaging apparatus 100 will be set. That is, even if the AEC sensor 210 which is the existing AEC system is removed after the setting, an image having pixel output values aimed as a radiation image will be obtained from the radiation imaging apparatus 100.

Note that, although the example illustrated in FIG. 1 which has the configuration including the standing position stand 200 is described as the radiation imaging system 10, the radiation imaging system 10 is not limited to this, and may have a configuration including, for example, a fluoroscopy table. Additionally, in the example illustrated in FIG.

6, although the setting of the threshold value by the AEC on the radiation imaging apparatus 100 side is performed immediately before the end of the flowchart illustrated in FIG. 6, the setting is not limited to this. For example, the setting of the threshold value by the AEC on the radiation imaging apparatus 100 side may be performed for each imaging protocol so as to achieve the same object.

In the first embodiment described above, the threshold value related to the automatic exposure control (AEC) in the second radiation imaging in which the AEC by the radiation detector 110 is performed after the first radiation imaging in which the AEC of the radiation R by the AEC sensor 210 is performed is set as follows. Specifically, in the first embodiment, the threshold value related to the AEC in the second radiation imaging is set based on the pixel values in the plurality of pixels of the radiation detector 110 at the time when the irradiation of the radiation R by the radiation generating apparatus 240 is stopped in the first radiation imaging (step S608 of FIG. 6). Then, when the processing proceeds to the second radiation imaging, in a case where the dose value of the radiation R that is incident on the radiation detector 110 reaches the set threshold value, the radiation generating apparatus controlling unit 164 performs the threshold value reached notification to the radiation generating apparatus 240.

According to such a configuration, in the radiation imaging system 10 that performs the automatic exposure control (AEC) of the radiation, the automatic exposure control by the AEC sensor 210 can be reflected to the automatic exposure control by the radiation detector 110 with high accuracy. Accordingly, the AEC setting according to the existing AEC sensor 210 can be taken over to the radiation imaging apparatus 100, even in various combinations of the manufacturer of the radiation generating apparatus 240 and the manufacturer of the radiation imaging apparatus 100 (for example, when the manufacturers of the respective apparatuses are different).

Second Embodiment

Next, the second embodiment of the present invention will be described. Note that, in the description of the second embodiment set forth below, a description is omitted for the matters in common with the above-described first embodiment, and a description of the matters different from the above-described first embodiment will be made.

The schematic configuration of a radiation imaging system according to the second embodiment is the same as the schematic configuration of the radiation imaging system 10 according to the first embodiment illustrated in FIG. 1. Additionally, the internal configuration of the radiation imaging apparatus 100 according to the second embodiment is the same as the internal configuration of the radiation imaging apparatus 100 according to the first embodiment illustrated in FIG. 2. In addition, the arrangement example of the plurality of regions of interest (ROI) that are set in the pixel array 110a, which is the imaging region of the radiation detector 110 in the first embodiment illustrated in FIG. 3, can also be applied in the second embodiment. Further, the internal configuration of the imaging apparatus controlling unit 160 according to the second embodiment is the same as the internal configuration of the imaging apparatus controlling unit 160 according to the first embodiment illustrated in FIG. 4.

The above-described first embodiment has the mode in which the threshold value related to the AEC in the second radiation imaging is set based on the pixel values related to the electric signals obtained in the plurality of pixels of the radiation detector 110 for each radiation image obtained in the first radiation imaging. On the other hand, the second embodiment has a mode in which the threshold value related to the AEC in the second radiation imaging is set based on the pixel values related to the electric signals obtained in the plurality of pixels of the radiation detector 110, for each predetermined time period shorter than the obtaining time period of a radiation image in the first radiation imaging.

Additionally, the above-described first embodiment has the mode in which the automatic exposure control (AEC) function of the radiation by the radiation detector 110 is merely set to OFF at the time of the first radiation imaging (step S602 of FIG. 6). On the other hand, in the second embodiment, specifically, a mode will be illustrated in which, among the above-described AEC functions, the dose value detecting function is set to ON, and the threshold value reached notifying function is set to OFF at the time of the first radiation imaging.

FIG. 7 is a flowchart for illustrating an example of the processing procedure in a control method of the radiation imaging system 10 according to the second embodiment of the present invention.

Note that, similar to the above-described flowchart illustrated in FIG. 6, the flowchart illustrated in FIG. 7 may be implemented by the serviceman, when introducing the AEC function on the new radiation imaging apparatus 100 side into the existing AEC system. First, an AEC setting flow on the radiation imaging apparatus 100 side is selected via the input apparatus 330 by the operator S as the serviceman. This selection of the AEC setting flow is generally provided in a menu for servicemen.

When the AEC setting flow is started, in step S701 of FIG. 7, the controlling apparatus 310 notifies the radiation imaging apparatus 100 that the AEC setting flow is started.

Subsequently, in step S702, for example, the controlling apparatus 310 sets the automatic exposure control (AEC) function of the radiation R by the AEC sensor 210, which is the existing AEC system, to ON. Further, in step S702, for example, the controlling apparatus 310 sets the automatic exposure control (AEC) function of the radiation R by the radiation detector 110 of the radiation imaging apparatus 100 to OFF. Here, in the second embodiment, when setting the AEC function by the radiation detector 110 to OFF, the above-described dose value detecting function is set to ON, and the above-described threshold value reached notifying function is set to OFF.

When the setting in step S702 is performed, the processing of radiation imaging (first radiation imaging) in which the automatic exposure control (AEC) by the AEC sensor 210 is performed is started. Specifically, first, in step S703, for example, the controlling apparatus 310 selects an imaging protocol, which is a target of the existing AEC (the automatic exposure control by the AEC sensor 210), based on the information that is input by the operator S via the input apparatus 330. On this occasion, the imaging site information of the subject H is included in the imaging protocol. Then, according to the set imaging protocol, frame rate setting information, sensitivity setting information, and so on are transmitted to the radiation imaging apparatus 100 as an imaging mode. Also, in step S703, for example, the radiation generating apparatus 240 sets the irradiation conditions of the radiation R, based on the information that is input by the operator S via the console 350. On this occasion, the setting of the tube voltage and tube current of the radiation source 250, irradiation time timeout setting and so on are included in the irradiation conditions.

Subsequently, in step S704, the radiation generating apparatus 240 irradiates the radiation R from the radiation source 250, based on the irradiation conditions, etc. that are set in step S703. Thereafter, when the accumulated value of an analog signal from the existing AEC sensor 210 reaches a predetermined threshold value, the radiation generating apparatus 240 stops the irradiation of the radiation R from the radiation source 250.

Subsequently, in step S705, the radiation imaging apparatus 100 stores, in the memory 163, pixel values related to electric signals in the plurality of pixels of the radiation detector 110 at the time when the irradiation of the radiation R by the radiation generating apparatus 240 is stopped. On this occasion, the radiation imaging apparatus 100 stores, in the memory 163, the pixel values of the plurality of pixels included in one or more selected regions of interest (ROI), for each predetermined time period shorter than the obtaining time period of a radiation image in the first radiation imaging (for example, in real time). Note that the pixel values stored in the memory 163 here correspond to the dose detection value, which is the accumulated value of the dose (arrived dose) detected in the predetermined time period in the plurality of pixels included in the one or more selected regions of interest. However, in the second embodiment, since the threshold value reached notifying function of the radiation imaging apparatus 100 is set to OFF in step S702, the irradiation stop of the radiation R is not performed by the action on the radiation imaging apparatus 100 side.

Subsequently, in step S706, similar to step S606 of FIG. 6, for example, the radiation imaging apparatus 100 determines whether or not a predetermined number of times of radiation imaging is completed. As a result of this determination in step S706, if the predetermined number of times of radiation imaging is not completed (step S706/NO), the processing returns to step S704, and step S704 and the subsequent processing are performed again.

On the other hand, as the result of the determination in step S706, if the predetermined number of times of radiation imaging is completed (step S706/YES), the processing proceeds to step S707.

When the processing proceeds to step S707, similar to step S607 of FIG. 6, for example, the radiation imaging apparatus 100 or the controlling apparatus 310 determines whether or not the selection of the target imaging protocol is completed. As a result of this determination in step S707, if the selection of the target imaging protocol is not completed (step S707/NO), the processing returns to step S703, and step S703 and the subsequent processing are performed again.

On the other hand, as the result of the determination in step S707, if the selection of the target imaging protocol is completed (step S707/YES), the processing proceeds to step S708. When the processing proceeds to step S708, the radiation imaging apparatus 100 sets the pixel value (dose detection value) in the imaging mode corresponding to each imaging protocol stored in the memory 163 in step S705 as the threshold value in the automatic exposure control of the radiation R by the radiation detector 110. This threshold value set in step S708 is the threshold value used in the second radiation imaging in which the automatic exposure control of the radiation R by the radiation detector 110 is performed after the first radiation imaging in which the automatic exposure control by the AEC sensor 210 is performed. This processing in step S708 is performed in, for example, the configuration unit of the radiation imaging apparatus 100, such as the CPU 162 or the radiation generating apparatus controlling unit 164. Then, the configuration unit (the CPU 162 or the radiation generating apparatus controlling unit 164) of the radiation imaging apparatus 100 that performs this setting of the threshold value in step S708 configures the "threshold value setting unit".

Then, when the processing proceeds to the second radiation imaging, in a case where the dose value of the radiation R that is incident on the pixel array 110a (the selected region of interest) reaches the threshold value that is set in step S708, the radiation generating apparatus controlling unit 164 performs the threshold value reached notification to the radiation generating apparatus 240. The radiation generating apparatus controlling unit 164 that performs this threshold value reached notification configures the "notifying unit".

When the processing in step S708 is completed, the processing of the flowchart illustrated in FIG. 7 is ended.

In this second embodiment, when different drive control is performed for the AEC driving of the radiation imaging apparatus 100 for calculating the dose detection value, and the normal image signal output driving of the pixels, the accuracy of the setting of the threshold value related to the AEC is further improved. Accordingly, the AEC can also be performed in the AEC function of the newly introduced radiation imaging apparatus 100, under an irradiation dose condition of the radiation R equivalent to that in the automatic exposure control (AEC) by the AEC sensor 210 which is the existing AEC system.

According to the second embodiment, similar to the above-described first embodiment, in the radiation imaging system 10 that performs the automatic exposure control (AEC) of the radiation, the automatic exposure control by the AEC sensor 210 can be reflected to the automatic exposure control by the radiation detector 110 with high accuracy. Accordingly, the AEC setting according to the existing AEC sensor 210 can be taken over to the radiation imaging apparatus 100, even in various combinations of the manufacturer of the radiation generating apparatus 240 and the manufacturer of the radiation imaging apparatus 100 (for example, when the manufacturers of the respective apparatuses are different).

MODIFICATIONS

The above-described first and second embodiments have the mode in which the threshold value related to the AEC in the second radiation imaging is set based on the pixel values in the plurality of pixels of the radiation detector 110 at the time when the irradiation of the radiation R by the radiation generating apparatus 240 is stopped in the first radiation imaging. For example, a mode may be taken that can switch between the threshold value that is set in the above-described first and second embodiments, and the threshold value held in the radiation imaging apparatus 100, as the threshold value related to the AEC in the second radiation imaging, based on one of an instruction by the operator S and the subject information related to the subject. Here, a recommended value by the manufacturer of the radiation imaging apparatus 100, etc. can be listed as the threshold value held in the radiation imaging apparatus 100. Accordingly, whether to perform the control in line with the existing AEC system, or the control in line with the recommended value of the newly introduced radiation imaging apparatus 100 can be switched based on one of the instruction by the operator S and the subject information.

Additionally, in the above-described first and second embodiments, after reflecting the AEC function of the AEC sensor 210, which is the existing AEC system, to the AEC function of the newly introduced radiation imaging apparatus 100, the AEC sensor 210 may be detached or may be left attached as is. if the existing AEC sensor 210 is removed, the effect can be obtained that the actual irradiation dose to the subject H can be reduced by the radiation attenuation amount of the existing AEC sensor 210 at the time when the threshold value is reached. On the other hand, if the existing AEC sensor 210 is left attached as is, the AEC as before can be performed also in radiation imaging that does not use the radiation imaging apparatus 100, for the purpose of backup, etc.

According to each of the above-described embodiments and modifications, in the radiation imaging system that performs the automatic exposure control (AEC) of the radiation, the automatic exposure control by the AEC sensor can be reflected to the automatic exposure control by the radiation detector with high accuracy. In addition, even if it is difficult to provide a communication unit that obtains the AEC information due to the reason that the manufacturer of the radiation generating apparatus is different from the manufacturer of the radiation imaging apparatus, etc., the automatic exposure control information can be reflected with high accuracy. Additionally, even if the setting of the AEC information is adjusted in an old system, the automatic exposure control information can be reflected in a manner applicable to a new system.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)'), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-123016, filed Jul. 28, 2021, which is hereby incorporated by reference herein in its entirety.

What is claimed is:

1. A radiation imaging apparatus comprising:
a radiation detector including a pixel array in which a plurality of pixels being capable of detecting radiation as electric signals are arranged, the radiation transmitted through an AEC sensor used for performing automatic exposure control of radiation irradiated from a radiation generating apparatus;
a notifying unit configured to perform threshold value reached notification to the radiation generating apparatus, if a dose value of the radiation incident on the pixel array reaches a threshold value; and
a threshold value setting unit configured to set the threshold value in second radiation imaging in which automatic exposure control of the radiation by the radiation detector is performed after first radiation imaging in which the automatic exposure control of the radiation by the AEC sensor is performed, based on pixel values related to the electric signals detected by the plurality of pixels in the first radiation imaging.

2. A radiation imaging apparatus according to claim 1, wherein the threshold value setting unit is configured to set the threshold value in the second radiation imaging based on the pixel values related to the electric signals obtained in the plurality of pixels for each radiation image obtained in the first radiation imaging.

3. A radiation imaging apparatus according to claim 1, wherein the threshold value setting unit is configured to set the threshold value in the second radiation imaging based on the pixel values related to the electric signals obtained in the plurality of pixels for each predetermined time period shorter than an obtaining time period of a radiation image in the first radiation imaging.

4. A radiation imaging apparatus according to claim 1, wherein a region of interest including a plurality of pixels is provided in a part of a region of the pixel array, and
the threshold value setting unit is configured to set the threshold value in the second radiation imaging based on pixel values in the plurality of pixels included in the region of interest.

5. A radiation imaging apparatus according to claim 4, wherein a plurality of regions of interest are provided in the pixel array, and
the threshold value setting unit is configured to set the threshold value in the second radiation imaging based on the pixel values in the plurality of pixels included in the plurality of regions of interest.

6. A radiation imaging apparatus according to claim 1, further comprising:
an on/off setting unit configured to set ON/OFF of the automatic exposure control of the radiation by the radiation detector,
wherein the on/off setting unit is configured to set the automatic exposure control of the radiation by the radiation detector to OFF when the first radiation imaging is performed.

7. A radiation imaging apparatus according to claim 6, wherein, when setting the automatic exposure control of the radiation by the radiation detector to OFF, the on/off setting unit is configured to perform at least one setting of turning OFF a dose value detecting function of the radiation based on the pixel values in the plurality of pixels, and turning OFF a threshold value reached notifying function by the notifying unit based on the dose value detecting function.

8. A radiation imaging apparatus according to claim 7, wherein the on/off setting unit is configured to independently set turning OFF the dose value detecting function and turning OFF the threshold value reached notifying function.

9. A radiation imaging apparatus according to claim 7, wherein the on/off setting unit is configured to set the dose value detecting function to ON and set the threshold value reached notifying function to OFF when the first radiation imaging is performed.

10. A radiation imaging apparatus according to claim 1, wherein the threshold value in the second radiation imaging is switchable between a threshold value based on the pixel values related to the electric signals obtained in the plurality of pixels, and a threshold value held in the radiation imaging apparatus comprising the radiation detector, based on one of an instruction by an operator and subject information related to the subject.

11. A radiation imaging apparatus according to claim 1, wherein the pixel array includes a plurality of first pixels configured to detect the radiation as electric signals, and a plurality of second pixels configured to detect the radiation as electric signals with a sensitivity different from a sensitivity of the plurality of first pixels.

12. A radiation imaging apparatus according to claim 1, wherein the pixel values include an accumulated value of the electric signals detected by the plurality of pixels.

13. A radiation imaging apparatus according to claim 1, wherein the threshold value setting unit is configured to set the threshold value in the second radiation imaging based on the pixel values related to the electric signals in the plurality of pixels when irradiation of the radiation by the radiation generating apparatus is stopped in the first radiation imaging.

14. A radiation imaging system comprising:
a radiation imaging apparatus according to claim 1;
a controlling apparatus connected with the radiation imaging apparatus and the radiation generating apparatus, and configured to control the radiation imaging apparatus and the radiation generating apparatus.

15. A control method of a radiation imaging apparatus comprising a radiation detector including a pixel array in which a plurality of pixels being capable of detecting radiation as electric signals are arranged, the radiation transmitted through an AEC sensor used for performing automatic exposure control of radiation irradiated from a radiation generating apparatus, the control method comprising:
a notifying step for performing threshold value reached notification to the radiation generating apparatus, if a dose value of the radiation incident on the pixel array reaches a threshold value; and
a threshold value setting step for setting the threshold value in second radiation imaging in which automatic exposure control of the radiation by the radiation detector is performed after first radiation imaging in which the automatic exposure control of the radiation by the AEC sensor is performed, based on pixel values related to the electric signals detected by the plurality of pixels in the first radiation imaging.

* * * * *